United States Patent [19]
Edelstein

[11] Patent Number: 5,591,179
[45] Date of Patent: Jan. 7, 1997

[54] ANASTOMOSIS SUTURING DEVICE AND METHOD

[75] Inventor: Robert A. Edelstein, Boston, Mass.

[73] Assignee: Applied Medical Resources Corporation, Laguna Hills, Calif.

[21] Appl. No.: 424,958

[22] Filed: Apr. 19, 1995

[51] Int. Cl.⁶ .................................................. A61B 17/00
[52] U.S. Cl. .......................... 606/144; 606/148; 606/153; 112/169
[58] Field of Search ............................. 606/1, 139, 144, 606/145, 147, 148, 149, 151, 153, 154, 155, 156, 222–223; 112/169, 80.03, 80.06; 604/106, 107; 223/102, 104

[56] References Cited

U.S. PATENT DOCUMENTS

| | | |
|---|---|---|
| 2,547,758 | 3/1951 | Keeling . |
| 3,168,092 | 2/1965 | Silverman . |
| 3,254,651 | 6/1966 | Collito . |
| 3,626,947 | 12/1971 | Sparks . |
| 3,669,099 | 6/1972 | Silverman . |
| 4,352,926 | 10/1982 | Matsuoka et al. . |
| 4,553,543 | 11/1985 | Amarasinghe ............ 606/153 |
| 4,578,061 | 3/1986 | Lemelson ............ 604/164 |
| 4,752,024 | 6/1988 | Green et al. . |
| 4,848,367 | 7/1989 | Avant et al. . |
| 4,873,977 | 10/1989 | Avant et al. . |
| 4,905,693 | 3/1990 | Ravo . |
| 4,911,164 | 3/1990 | Roth . |
| 4,994,066 | 2/1991 | Voss . |
| 5,047,039 | 9/1991 | Avant et al. ............ 606/153 |
| 5,053,043 | 10/1991 | Gottesman et al. . |
| 5,254,126 | 10/1993 | Filipi et al. ............ 606/148 |
| 5,364,408 | 11/1994 | Gordon ............ 606/148 |
| 5,391,174 | 2/1995 | Weston ............ 606/148 |

FOREIGN PATENT DOCUMENTS

WO93/13714 7/1993 WIPO ............ 606/148

OTHER PUBLICATIONS

Brochure: North American Medical, Inc.; "The DDV Ligator has many points to consider", pp. 1–10; Lubbock, Texas.

Primary Examiner—Michael Powell Buiz
Assistant Examiner—Jeffrey A. Schmidt
Attorney, Agent, or Firm—Richard L. Myers

[57] ABSTRACT

A surgical suturing device comprises an elongate body having an axis extending between a proximal end and a distal end. A lumen of the body has a generally axial portion and a transverse portion which extends laterally and is adapted to receive a needle and associated suture. An elongate deployment member is disposed in the axial portion of the lumen and biased to a proximal position. The deployment member is movable to a distal portion to expel the needle and suture from the lumen through tissue surrounding the device. An associated method for operating the device includes the steps of deploying the needle and suture from the lumen, moving the device distally to expose the empty transverse lumen, and reloading the lumen with a second needle and suture.

18 Claims, 5 Drawing Sheets

ANASTOMOSIS SUTURING DEVICE AND METHOD

BACKGROUND OF THE INVENTION

1. Field of the Invention

This invention relates generally to surgical devices which facilitate the suturing of tissue, and particularly conduit suturing.

2. Description of the Prior Art

Most body conduits are generally cylindrical in configuration and have a circular cross-section. When it is desirable to suture such a conduit, typically for attachment to another body conduit, the sutures are placed around the circumference of the conduit in order to maintain the patency of its lumen or channel. This type of attachment is commonly referred to as an anastomosis. It differs from straight line suturing in that each suture has a different orientation which is based on its position around the cross-sectional circumference of the conduit. It can be appreciated that some of the sutures are easily made from on top of the conduit, while others are more difficult to complete as they are beneath the conduit.

The complexity of anastomosis attachment is dramatically represented in a surgical procedure referred to as a radical retropubic prostatectomy. This is a well established surgical procedure for patients with localized prostatic carcinoma. In its broadest sense, this surgical procedure requires removal of the prostate gland after severing the gland from the bladder neck and the urethra. It is the attachment of the urethra stump to the bladder neck which is particularly difficult. This difficulty is complicated by the tendency of the urethral stump to retract into adjacent tissue. As a result, considerable time and effort must be extended to re-expose the urethra stump and begin the re-anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 4,911,164, Roth discloses the suture guide with a curved distal portion. This distal portion has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck. The aggressive nature of these extended members has caused considerable damage to the urethral stump.

U.S. Pat. No. 5,047,039 issued to Avant et al. discloses a surgical device for the ligation of dorsal vein and subsequent anastomosis. This device contains a pair of enclosed needles with attached suture which may be driven from the shaft of the device into adjacent tissue. The device does not facilitate placement of a plurality of sutures around an enlarged conduit such as the urethral stump. Nor does it in any way facilitate advancement of the urethral stump to increase its exposure. Various other needle guides, sounds and other suturing devices are disclosed in the following patents:

| | | |
|---|---|---|
| 2,547,758 | 3,669,099 | 4,848,367 |
| 3,168,092 | 4,352,926 | 4,905,693 |
| 3,254,651 | 4,553,543 | 4,994,066 |
| 3,626,947 | 4,752,024 | 5,053,043 |
| | 4,873,977 | |

In general, none of these devices of the prior art addresses the problem associated with re-anastomosis of the urethral stump to the bladder neck. Nor do they disclose any device which can accurately position a needle and suture combination for use at or near the severed end of a body conduit. Importantly, these devices are not flexible and accordingly do not enable the surgeon to assume the best operative position.

SUMMARY OF THE INVENTION

The present invention overcomes these difficulties of the prior art by providing an anastomosis suturing device which facilitates placement of an enclosed needle through anastomotic tissue with equal ease regardless of the position around the cross-sectional circumference. Once the sutures have been placed on one of the body conduits, and extended through the other conduit, they can be used to facilitate approximation. A particular embodiment of the invention is adapted for radical retropubic prostatectomy by providing a smooth rather than radical mechanism for exposing the urethral stump. Then the needle can be deployed by operation of the proximal end of the device through the tissue.

The suturing device includes a shaft with portions defining an interior channel extending between the proximal and distal ends of the shaft. This channel includes a generally axial lumen which extends to the proximal end and a generally transverse lumen which extends from the axial lumen distally outwardly to an exit hole at the outer surface of the shaft. The needle and suture can be backloaded into the transverse lumen of the channel while a generally non-compressible member can be movably mounted in the axial lumen of the channel. At the proximal end of the shaft a handle is provided with means operative to push the member distally through the lumen to deploy or expel the needle.

In operation, the distal end of the device is moved through the first conduit, such as the urethral stump. Traction means, which can be in the form of an annular flange having a rounded non-traumatic outer surface, tends to elongate the stump for increased exposure, viewing and suturing. With the device and the tissue in this operative position, the non-compressible member can be moved distally, by operation of the handle of the device, deploying the needle from the transverse lumen and through the tissue at the end of the distal conduit. The needle can then be removed leaving the suture in place.

After the initial suture has been placed, the device can be advanced from the conduit in order to expose the exit hole of the transverse lumen at the distal end of the device. An additional needle and suture can be backloaded into the transverse lumen and the device retracted back into the conduit, such as the urethral stump. Axially rotating the device, either before or after retraction, will orient the exit hole of the transverse lumen at a new radial location where the handle can again be operated to expel the additional needle from the transverse lumen and through the tissue.

This procedure can be repeated until the full circumference of the conduit has been sutured. At this point each of the sutures can be attached to the second conduit, such as the bladder neck. In this step of the procedure, the device including the enlarged traction member can be used to move the urethral stump into approximation with the bladder neck. As the two ends of each suture are brought together, the conduits are moved into surgically contacting relationship where the respective sutures can be tied to complete the anastomosis. The suturing device can then be removed from the conduits.

In one aspect of the invention, a surgical suturing device includes an elongate body having a lumen, an outer surface and an axis extending between a proximal end and a distal end. Portions of the body define a lumen having a generally axial portion extending to the proximal end of the body and a transverse portion extending distally from the axial portion and exiting the body through the outer surface. The transverse portion of the lumen is sized and configured to receive a needle and a suture attached to the needle. Means is disposed in the axial portion of the lumen and movable through the lumen for deploying the needle and suture.

Another aspect of the invention includes a method for attaching a first body conduit to a second body conduit. The second conduit is defined by tissue having a first end and a second end. This method includes the steps of providing a suturing device having an elongate shaft having an outer surface, the shaft defining at least one lumen having a generally axial portions at a proximal end of the lumen and a transverse portion extending from the axial portion at a distal end of the lumen. The transverse portion exits the device through an exit hole at the outer surface of the body. A needle having a sharp tip and an attached suture is loaded into the lumen. Then the distal end of the suturing device is inserted into the first end of the second conduit and through the second conduit to the second end of the second conduit. The method further comprises the step of deploying the needle from the lumen and through the exit hole into the tissue at the second end of the second conduit. Then the suture can be connected to the first body conduit to attach the first conduit to the second conduit.

In a further aspect, the invention comprises a method for suturing tissue forming a circumferential free end of a body conduit. The method includes the steps of providing a suturing device having an elongate shaft and portions defining a lumen extending through an exit hole at the outer surface of the shaft. A first needle and attached suture is loaded into the lumen of the device and the device inserted into the body conduit to an operative site where the tissue of the body conduit covers the exit hole. The first needle can then be issued from the lumen to engage the surrounding tissue. The device is then advanced distally to expose the exit hole and the lumen is reloaded with an additional needle and attached suture. The device can then be retracted proximally to a new operative site where the tissue of the body conduit covers the exit hole. Deploying the second needle from the lumen at the new operative site results in placement of a second suture around the circumferential free end of the conduit. Repeating the advancing, reloading, retracting and deploying steps around the entire circumference of the conduit facilitates the suturing method.

These and other features and advantages of the invention will become more apparent with a discussion of preferred embodiments and method steps, and reference to the associated drawings.

DESCRIPTION OF PREFERRED EMBODIMENTS AND BEST MODE OF THE INVENTION

Figure 1:
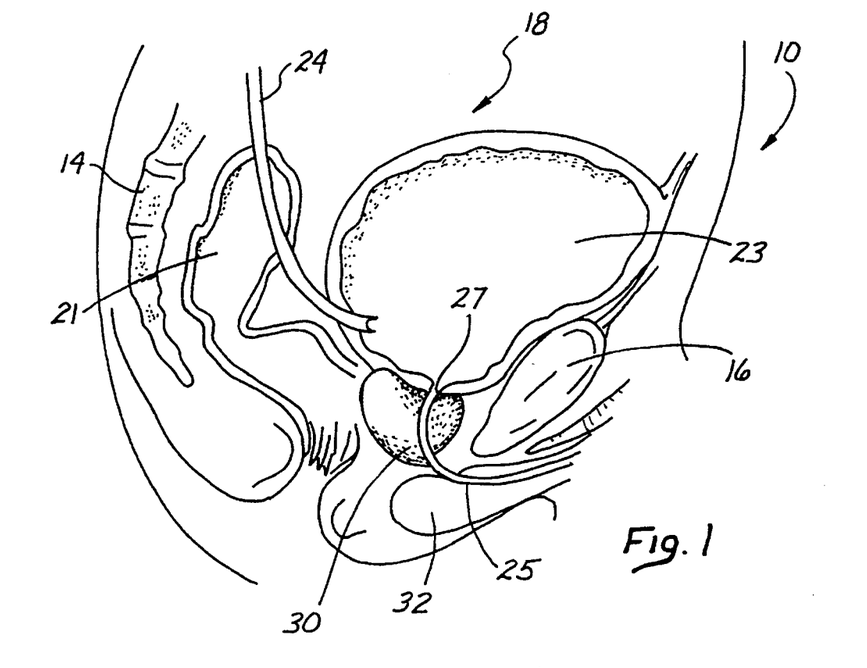
FIG. 1 is a schematic view, partially in section illustrating the pelvic region of a male body including a bladder, prostate, and urethra.

In the perspective view of FIG. 1, a pelvic region of the male anatomy is designated by the reference numeral 10. This region is defined left to right in FIG. 1, between a backbone 14 and a pelvic bone 16. Between these two bones, 14, 16, an abdominal cavity 18 includes an intestine 21 and a bladder 23. A ureter 24 extends from the kidneys (not shown) to provide an inlet to the bladder 23. The conduit providing an outlet for the bladder 23 is commonly referred to as a urethra 25 which extends from a bladder neck 27 to regions exterior of the body.

Figure 2:
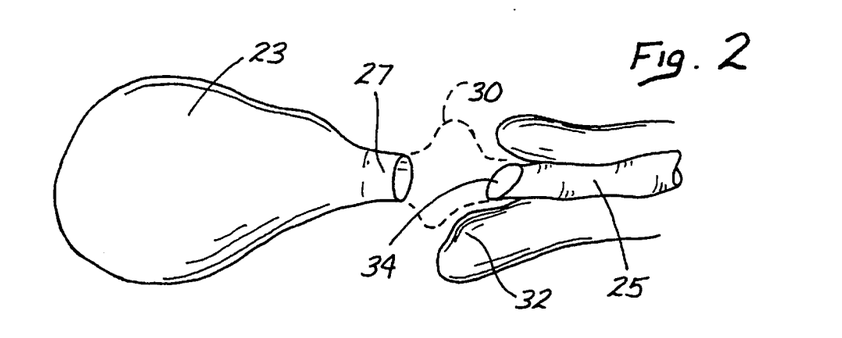
FIG. 2 is a perspective view of a urethral stump and bladder neck positioned for anastomotic attachment in a radical retropubic prostatectomy surgical procedure.

Between the bladder neck 27 and the exterior regions, the urethra 25 is defined in part by a prostate gland 30. In a surgical procedure referred to as a radical prostatectomy, it is the prostate gland 30 which is removed. This procedure is best illustrated in FIG. 2 which shows the bladder 23, the bladder neck 27, the urethra 25, and surrounding tissue 32. The prostate gland 30 is shown by dotted lines indicating that the gland has been removed leaving a first conduit, in the form of the bladder neck 27, and a second conduit, in the form of the urethra 25, for anastomotic reattachment. The exposed end of the urethra 25 is commonly referred to as the urethral stump 34.

In this particular procedure, it is unfortunate that the removal of the prostate 30 causes the urethral stump 34 to withdraw into the surrounding tissue 32. This not only renders the urethra 25 somewhat inaccessible, but also demands that the suturing of the stump 34 be accomplished in a difficult position with a surgeon having to work around the pelvic bone 16.

Figure 3:
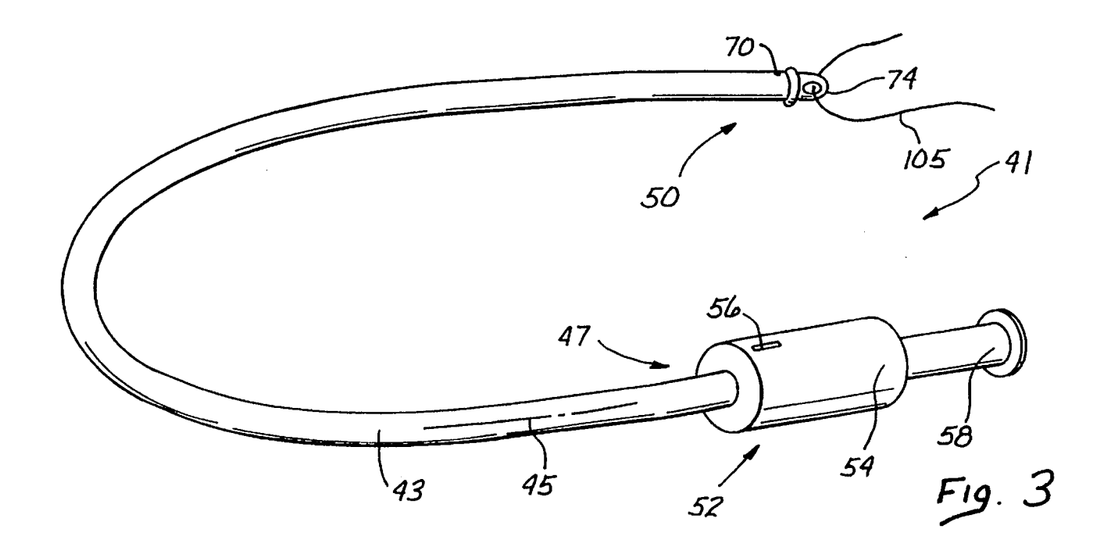
FIG. 3 is a perspective view of one embodiment of an anastomotic suturing device of the present invention.

A suturing device of particular value to this surgery is illustrated in FIG. 3 and designated by the reference numeral 41. Although the device 41 offers significant advantages to a prostatectomy procedure, it will be understood that the device is applicable for use in any anastomosis procedure where the end of a conduit is to be sutured to a second conduit. The device 41 includes an elongate shaft 43 having an axis 45 extending between a proximal end 47 and a distal end 50. A handle 52 disposed at the proximal end 47 includes a housing 54 and an indicator 56 which facilitates radial alignment of the device 41. A plunger 58, operable typically by the thumb of the surgeon, is movable between a proximal position and a distal position in the manner described in greater detail below.

Figure 4:
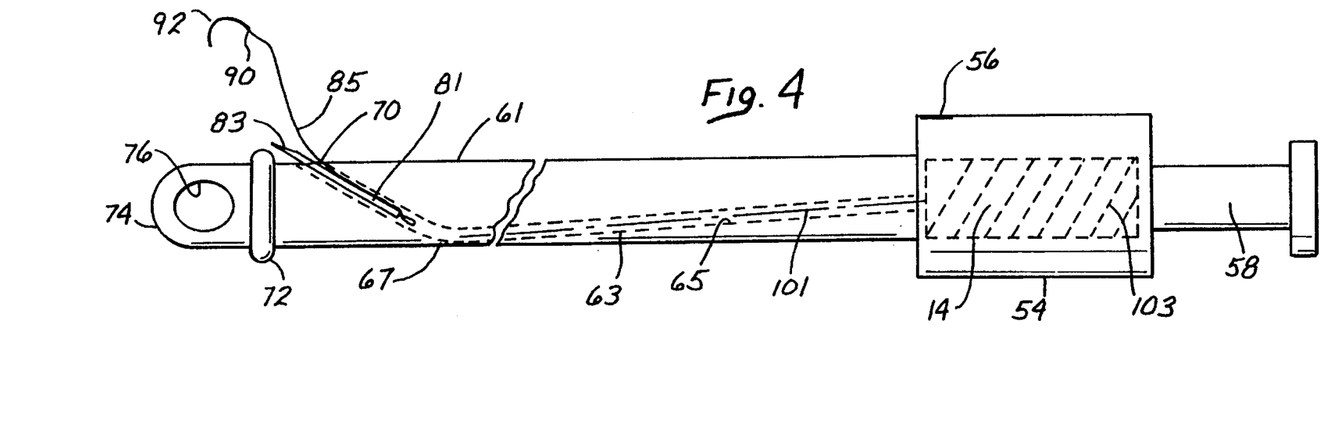
FIG. 4 is a side elevation view of the device illustrated in FIG. 3.

Referring now to the enlarged view of FIG. 4, it can be seen that the shaft 43 has an outer surface 61 and an interior channel 63 which extends generally from the distal end 50 to the proximal end 47. In a preferred embodiment, the channel 63 includes an axial lumen 65 which extends into a transverse lumen 67 of particular interest to the present invention. The axial lumen 65 extends generally axially of the shaft 43 from the proximal end 47. At its distal end, the axial lumen 65 communicates with the transverse lumen 67 which is disposed generally transverse to the axis 45. In a preferred embodiment the transverse lumen 67 extends from the axial lumen 65 distally radially outwardly to an exit hole 70 at the outer surface 61. The channel 63 of the shaft 43 is best illustrated in the enlarged cross-section view of FIG. 5.

Figures 5, 6, 7:
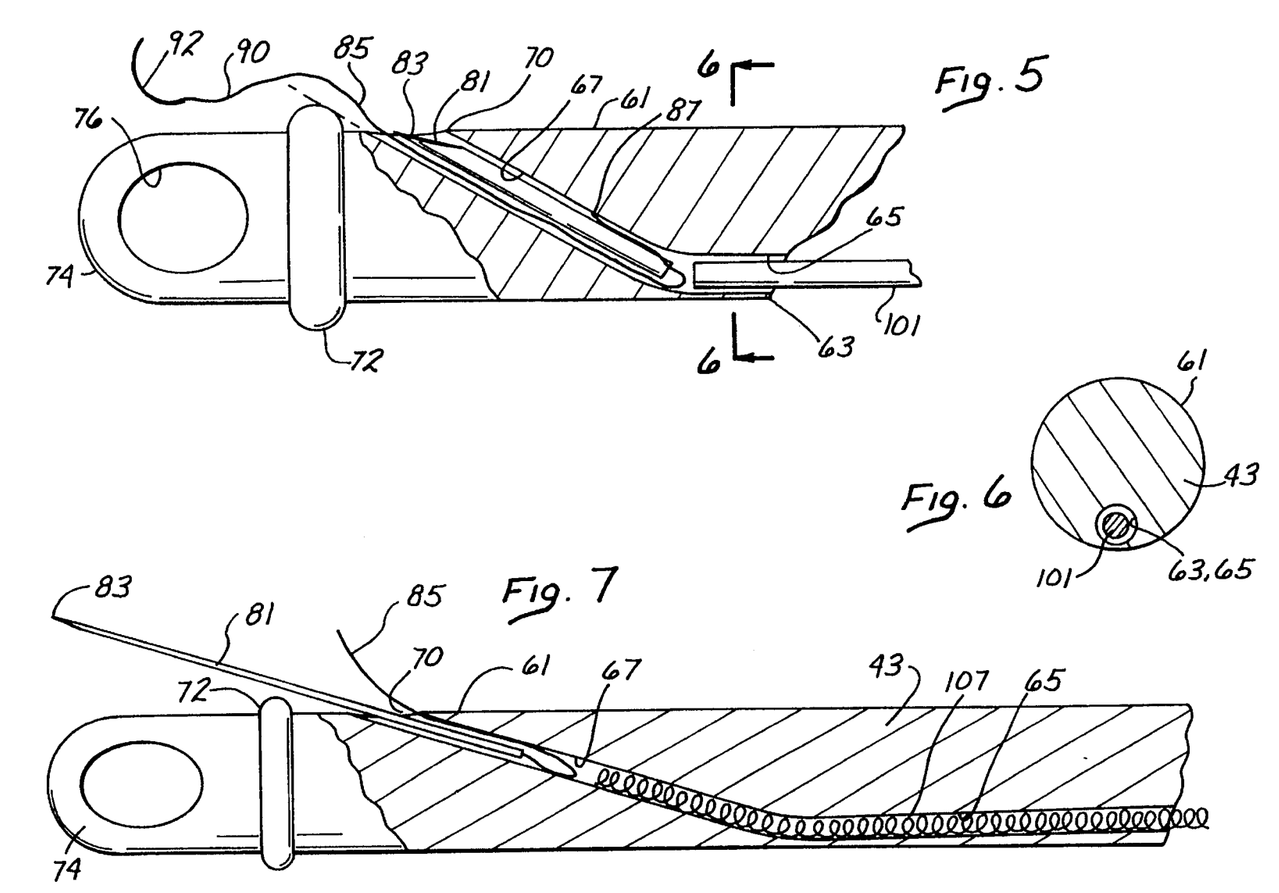
FIG. 5 is an enlarged side view partially in section of a distal region of the device illustrated in FIG. 3.
FIG. 6 is a radial cross-section view taken along lines 6—6 of FIG. 5.
FIG. 7 is a side elevation view similar to FIG. 5 and illustrating a further embodiment of the invention.

Disposed distally of the exit hole 70 is an annular flange 72 which in the illustrated embodiment extends outwardly of the surface 61 perpendicular or at least transverse to the axis 45. This flange 72 provides traction means for engaging the conduit to be sutured in a manner described in greater detail below. The device 41 is also provided with an attachment member 74 which, in the illustrated case, defines a hole 76.

In operation, a needle 81 having a sharp tip 83 and attached suture 85 is backloaded into the transverse lumen 67. The suture 85 has an end 87 which is generally free, and an end 90 which is commonly provided with a needle 92 in the form of a hook. With the needle 81 loaded into the transverse lumen 67, it is the purpose of the device 41 to launch, deploy or otherwise expel the needle 81 from the lumen 67. This is accomplished in the preferred embodiment by a generally non-compressible member 101, which is shown in FIG. 4 but best illustrated in the enlarged cross-sectional view of FIG. 5. This non-compressible member 101 is movable through the channel 63 by operation of the plunger 58 to move the needle 81 from the lumen 67. In the illustrated embodiment, this requires that the non-compressible member 101 include portions which are sufficiently flexible to negotiate the transition between the axial lumen 65 and the transverse lumen 67.

In order to facilitate backloading of the needle 81 into the transverse lumen 67, the plunger 58, with the attached non-compressible member 101, is biased to its proximal position by a spring 103 which can be disposed in the housing 54. Then, by operation of the plunger 58 against the bias of the spring 103, the non-compressible member 101 can be moved distally within the channel 63 to engage the needle 81. Further operation of the plunger 58 to move the non-compressible member 101 distally will force the needle from the transverse lumen 67 through the exit hole 70. The non-compressible member 101 will typically be formed from stainless steel with characteristics sufficient to achieve axial bending without substantial axial compression. In an alternate embodiment of the invention, the non-compressible member 101 is formed from a spring 107 as illustrated in FIG. 7. The spring 107 not only provides the desirable non-compressible characteristics but also the bending characteristics required in the preferred embodiment, to negotiate transition between the lumens 65 and 67.

A further discussion of an anastomosis procedure using the device 41 will be illustrated and discussed with reference to a prostatectomy procedure wherein the bladder neck 27 and the urethral stump 34 form the conduits to be joined. It will be understood however that these conduits 27 and 34 are merely representative of any two body conduits which are to be joined in an anastomosis procedure.

Figure 8:
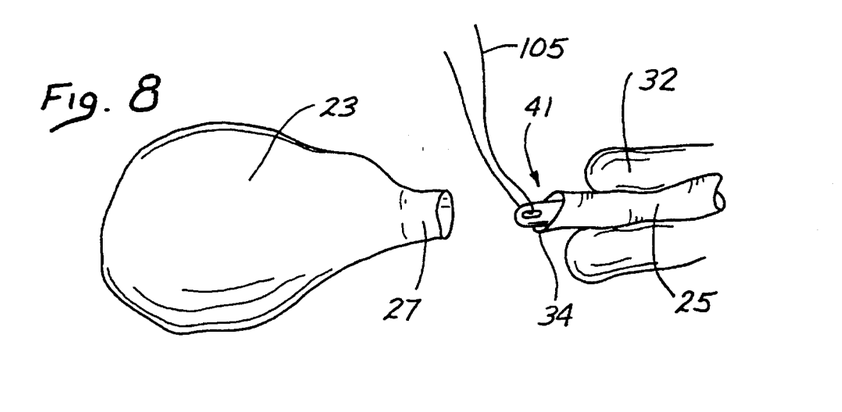
FIG. 8 is a side elevation view of the device operatively disposed in the urethral stump with a traction mechanism functioning to facilitate extension of the stump from surrounding tissue.

Referring now to FIG. 8, it can be seen that the device 41 is initially extended through one of the conduits, such as the urethra 25, until the distal end 50 of the device 41 extends through the end of the conduit, such as the ureteral stump 34. With the device 41 positioned to extend from the stump 34, the attachment member 74 will be exposed. In a typical procedure, this attachment member 74 can be engaged by a line 105 extending through the hole 76 and tied for example extracorporeally to initially elevate the urethral stump 34. This elevation tends to facilitate the suturing of the urethral stump 34.

As the device 41 is moved distally within the urethra 25, traction means in the form of the annular flange 72, frictionally engages the inner walls of the urethra 25 thereby stretching the urethra 25 to expose the urethral stump 34 from the surrounding tissue 32. It has been found that the annular flange 72 with a smooth outer surface provides sufficient friction to facilitate this exposure of the stump 34 without damaging the walls of the urethra 25.

Figure 9:
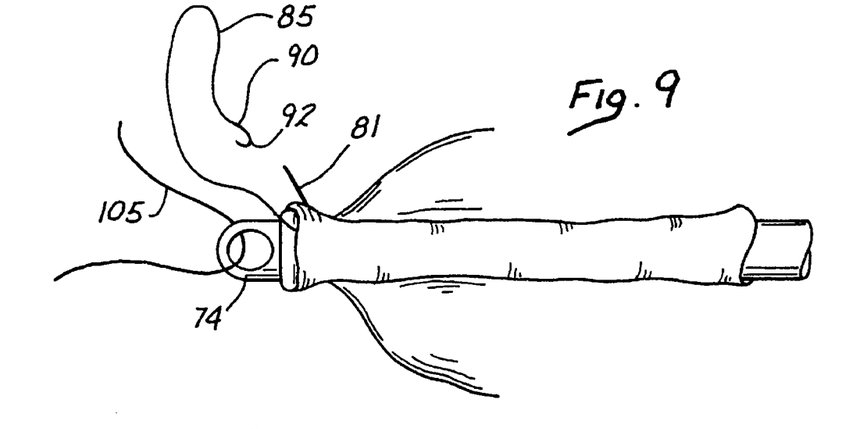
FIG. 9 illustrates a side elevation view similar to FIG. 8 with the needle partially deployed through the tissue of the urethral stump.
Figure 10:
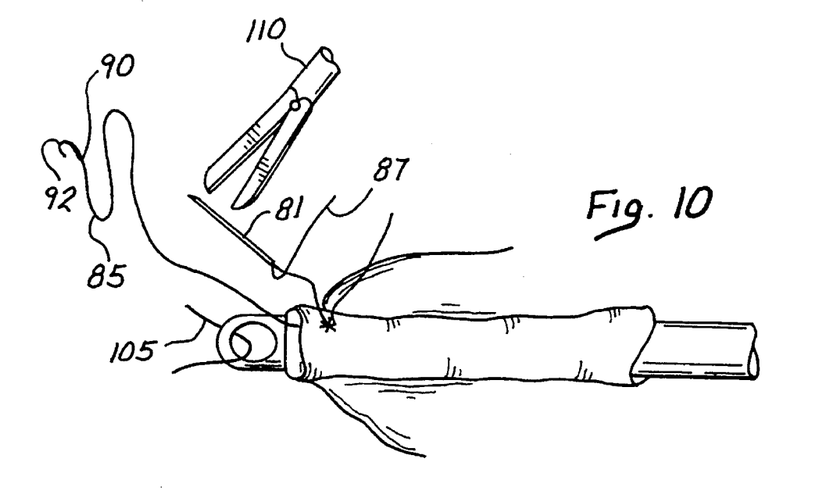
FIG. 10 is a side elevation view similar to FIG. 9 and illustrating the needle fully deployed leaving a suture extending through the tissue of the urethral stump.

With the device 41 operatively positioned, the urethral stump 34 will extend over the annular flange 72 covering the exit hole 70. Then, as the plunger 58 is operated and the non-compressible member 101 moves distally within the channel 63, the needle 81 will be expelled from the lumen 67 forcing the sharp tip 83 through the distal walls of the conduit, such as the urethral stump 34. This step of the procedure is best illustrated in FIG. 9. At this point, the needle 81 can be engaged by a grasper 110 thereby threading the suture 85 through the urethral stump 34. The needle 81 can then be withdrawn from the free end 87 of the suture 85 and removed from the operative site as best illustrated in FIG. 10.

Figure 11:
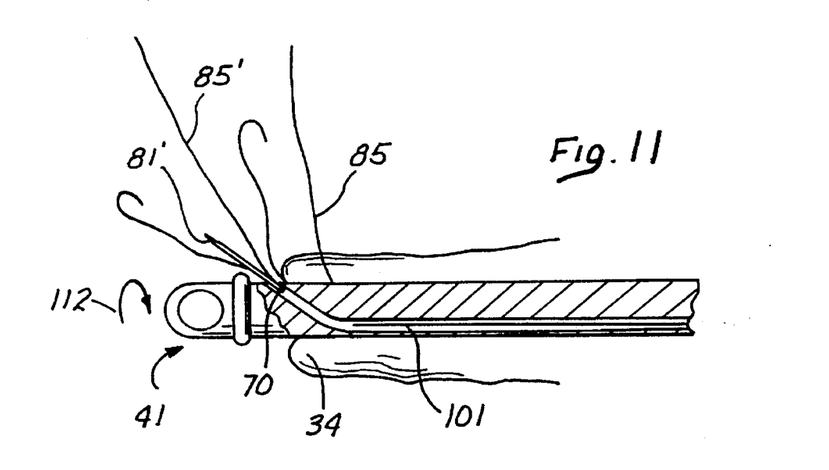
FIG. 11 is a side elevation view similar to FIG. 10 and illustrating the suturing device extending through the urethral stump to expose a transverse lumen of the device, and further illustrating the steps of loading an additional needle into the transverse lumen and axially rotating the device.
Figure 12:
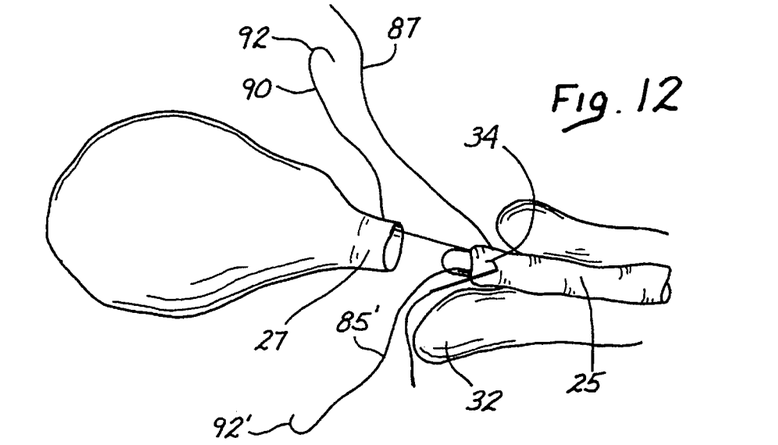
FIG. 12 is a side elevation view similar to FIG. 11 illustrating the step of withdrawing the device back into the urethral stump with the exit hole oriented at a new radial location.

At this point in the procedure, it is desirable to reload the device 41 so that an additional suture can be placed around the circumference of the urethral stump. In a preferred method, the device 41 is moved axially distally a distance sufficient to clear the exit hole 70 from the urethral stump 34. As illustrated in FIG. 11, this further distal movement of the device 41 may enable the urethral stump 34 to disengage the traction means formed by the annular flange 72 in order to expose the exit hole 70. With the exit hole 70 providing access to the transverse lumen 67, a second needle 81' and attached suture 85' can be backloaded into the transverse lumen 67. Once the additional needle 81' has been loaded, the device 41 can be drawn back to the operative position illustrated in FIG. 9.

In order that the additional suture 85' might be placed at a different location around the circumference of the urethral stump 34, it is desirable to axially rotate the device 41. This step can be accomplished while the device 41 is extended from the urethral stump 34, as illustrated in FIG. 11, and/or after the device 41 has been retracted back to its operative position. In the former case, the degree of axial rotation can be determined by viewing the position of the exit hole 70; in the latter case, one can view the position of the indicator 56 on the housing 54 at the proximal end 47 of the device 41. In both cases, the axial rotation of the device 41 is shown by the arrow 112 in FIG. 11.

Once the individual sutures, such as the sutures 85 and 85' have been positioned around the circumference of the urethral stump 34, the attachment of the sutures 85, 85' to the second conduit, such as the bladder neck 27 can be accomplished. In a preferred method, the hook-shaped needles 92 at the end 90 of each suture 85 can be engaged by a grasper and threaded through the bladder neck 27. Each needle 92 is inserted through the bladder neck 27 at a radial location appropriate to the position of the associated suture relative to the urethral stump 34.

Figure 13:
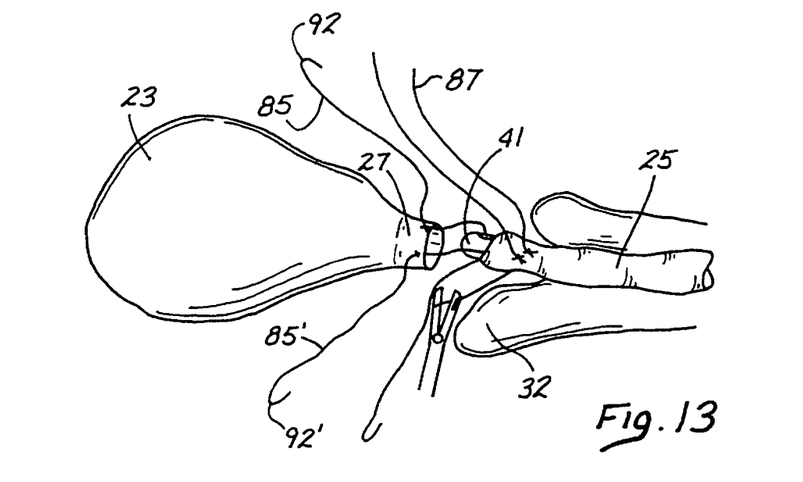
FIG. 13 is a perspective view similar to FIG. 1 illustrating the suture placement in both the urethral stump and the bladder neck.
Figure 14:
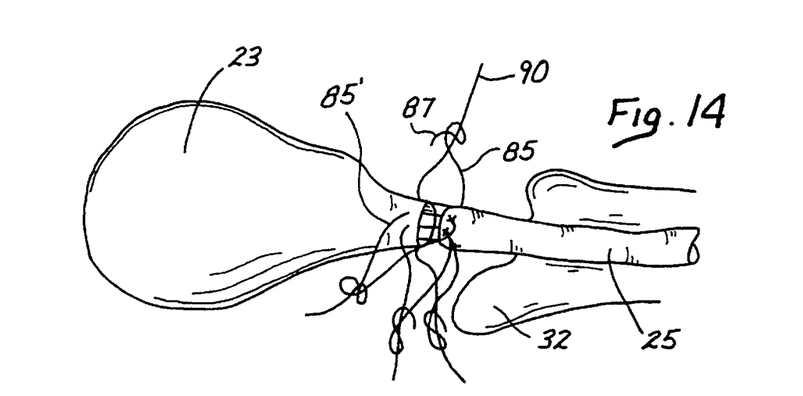
FIG. 14 is a perspective view similar to FIG. 13 showing the sutures drawn to approximate the urethral stump to the bladder neck.

Drawing the conduits 27 and 25 into approximation can be facilitated by the device 41 wherein the annular flange 72 maintains its frictional engagement of the urethra 25. Moving the device 41 distally stretches the urethra 25 into approximation with the bladder neck 27 as illustrated in FIG. 13. With the bladder neck 27 and the urethral stump 34 approximated, the individual sutures 85, 85' can be tied as illustrated in FIG. 14 to complete the anastomosis. The device 41 can then be removed from the conduit such as the urethra 25 and withdrawn from the operative site.

It will again be emphasized that the suturing device 41 and associated method are applicable to any anastomosis procedure wherein two conduits are to be joined in a manner facilitating fluid flow and patency. Although the specific device 41 illustrated has been discussed with reference to the bladder neck 27 and urethral stump 34, it will be appreciated with slight modifications of the device may make it even more applicable to other anastomosis procedures. For example, the annular flange 72 can take generally any shape as long as it provides some degree of traction with the associated conduit. If the annular shape is maintained, the outer surface of the flange 72 can be roughened or coated as required to achieve a particular degree of friction with the inner surface of the conduit.

Various implements can be substituted for the non-compressible member 101. Certainly the non-compressible characteristics will be of interest. Whether a particular non-compressible member also requires the ability to bend will depend on the relative orientation of the axial and transverse lumens 65 and 67, respectively.

Means other than the plunger 58 can also be provided to move the member 101 within the channel 63. For example, a thumb tab might be mounted on the housing 54 and attached through the wall of the housing 54 to engage the member 101. It is also conceivable that multiple needles could be disposed in the channel 63, each having its own suture 85. Operation of the non-compressible member 101 could then move the needles individually and sequentially through the exit hole 70 as the device 41 is rotated to achieve multiple circumferential positions for the deployment of each needle.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. A surgical suturing device comprising:

an elongate body having a lumen, an outer surface, and an axis extending between a proximal end and a distal end;

a handle disposed at the proximal end of the body;

portions of the body defining a lumen having a generally axial portion extending to the proximal end and a transverse portion extending distally from the axial portion and exiting the body through the outer surface of the body;

the transverse portion of the lumen exiting the elongate body at an exit hole at the outer surface of the body and being sized and configured to receive a needle and a suture attached to the needle;

attachment means disposed at the distal end of the elongate body distally of the exit hole; and means disposed in the axial portion of the lumen and movable through the lumen for deploying the needle and the suture from the lumen.

2. The surgical suturing device recited in claim 1 wherein the deploying means comprises:

an elongate flexible member movable between a first position and a second position, the member in the first position being disposed proximally within the lumen and in the second position being disposed distally within the lumen; and a spring disposed in the handle at the proximal end of the body and having properties for biasing the elongate member in the first position.

3. The surgical suturing device recited in claim 2 wherein the elongate member comprises a spring.

4. The surgical suturing device recited in claim 1 further comprising:

a traction mechanism in the form of an annulus extending radially outwardly of the outer surface at the distal end of the body.

5. The surgical suturing device recited in claim 3 wherein the transverse lumen exits the body through the outer surface proximally of the annulus.

6. A method for attaching a first body conduit to a second body conduit, the second conduit being defined by tissue and having a first end and a second end, the method comprising the steps of:

providing a suturing device having an elongate shaft with an outer surface, the shaft defining at least one lumen having a generally axial portion at a proximal end of the lumen and a transverse portion extending from the axial portion at a distal end of the lumen, the transverse portion exiting the device through an exit hole at the outer surface of the elongate shaft;

loading the lumen with a needle having a sharp tip and a suture attached to the needle;

inserting the distal end of the suturing device into the first end of the second conduit and through the second conduit to the second end of the second conduit;

deploying the needle from the lumen and through the exit hole into the tissue at the second end of the second conduit, in a direction generally toward the first conduit; and connecting the suture to the first body conduit to attach the first body conduit to the second body conduit.

7. The method recited in claim 6 wherein the needle is a first needle and the suture is a first suture, and the method further comprises the steps of:

moving the distal end of the device through the second end of the second conduit to expose the transverse portions of the lumen at the outer surface of the body;

reloading the transverse portion of the lumen with an additional needle having a sharp tip and an additional suture;

rotating the device to move the exit hole radially of the tissue at the second end of the second conduit; and moving the device proximally until the transverse lumen is covered by the tissue.

8. The method recited in claim 6 wherein the deploying step comprises the steps of:

positioning in the axial portion of the lumen a non-compressible longitudinal member; and moving the member distally within the axial portion of the lumen to deploy the needle from the transverse portion of the lumen.

9. The method recited in claim 6 further comprises the steps of:

providing the device with a traction mechanism in the form of an annulus extending radially outwardly of the outer surface distally of the exit hole; and during the inserting step stretching the second conduit distally with the traction mechanism.

10. The method recited in claim 9 wherein the needle is a first needle and the suture is a first suture, and the method further comprises the steps of:

moving the device distally through the second end of the second conduit to expose the traction mechanism and the exit hole;

reloading the transverse portions of the lumen with an additional needle having a sharp tip and an additional suture; and retracting the device proximally into the second end of the conduit until the transverse lumen and the traction mechanism is covered by the conduit.

11. A method of suturing tissue forming a free end of a body conduit, comprising:

providing a suturing device having an elongate shaft with an outer surface, the shaft defining at least one lumen having a generally axial portion at a proximal end of the lumen and a transverse portion extending from the axial portion of the lumen toward a distal end of the device and exiting the device through an exit hole at the outer surface of the device, said suturing device further having a traction mechanism in the form of an annular flange extending radially outwardly of the outer surface of the shaft;

advancing the suturing device within the body conduit until the traction mechanism is disposed at the free end of the conduit.

12. A method for suturing tissue forming a circumferential free end of a body conduit, comprising the steps of:

providing a suturing device having an elongate shaft and portions defining a lumen extending through an exit hole at an outer surface of the shaft;

loading a first needle and attached suture into the lumen of the suturing device;

inserting the device into a body conduit into an operative site where the tissue of the body conduit covers the exit hole;

issuing the first needle and attached suture from the lumen and through the tissue;

advancing the device distally to expose the exit hole;

reloading the lumen with an additional needle and attached suture;

retracting the device proximally to a new operative site where the tissue of the body conduit covers the exit hole; and deploying the second needle from the lumen at the new operative site.

13. The method recited in claim 12 further comprising the steps of:

repeating the advancing, reloading, retracting and deploying steps until the entire circumferential end of the conduit has been sutured.

14. A surgical suturing device comprising:

an elongate body having a lumen, an outer surface, and an axis extending between a proximal end and a distal end;

a handle disposed at the proximal end of the body;

portions of the body defining a lumen having a generally axial portion extending to the proximal end and a transverse portion extending distally from the axial portion and exiting the body through the outer surface of the body;

the transverse portion of the lumen being sized and configured to receive a needle and a suture attached to the needle;

means disposed in the axial portion of the lumen and movable through the lumen for deploying the needle and the suture from the lumen; and a traction mechanism in the form of an annulus extending radially outwardly of the outer surface at the distal end of the body.

15. The surgical suturing device recited in claim 14 wherein the transverse lumen exits the elongate body at an exit hole at the outer surface of the body, and the device further comprises:

attachment means disposed at the distal end of the elongate body distally of the exit hole.

16. The surgical suturing device recited in claim 14, wherein the transverse lumen exits the body through the outer surface proximally of the annulus.

17. The surgical suturing device recited in claim 14, wherein the deploying means comprises:

an elongate flexible member movable between a first position and a second position, the member in the first position being disposed proximally within the lumen and in the second position being disposed distally within the lumen; and a spring disposed in the handle at the proximal end of the body and having properties for biasing the elongate member in the first position.

18. The surgical suturing device recited in claim 17, wherein the elongate member comprises a spring.

* * * * *